US011123460B2

(12) United States Patent
Longo et al.

(10) Patent No.: US 11,123,460 B2
(45) Date of Patent: Sep. 21, 2021

(54) EMULSIONS OR MICROEMULSIONS FOR USE IN ENDOSCOPIC MUCOSAL RESECTIONING AND/OR ENDOSCOPIC SUBMUCOSAL DISSECTION

(71) Applicant: COSMO TECHNOLOGIES LTD., Dublin (IE)

(72) Inventors: Luigi Maria Longo, Lainate (IT); Luigi Moro, Lainate (IT); Enrico Frimonti, Lainate (IT); Alessandro Repici, Turin (IT)

(73) Assignee: COSMO TECHNOLOGIES LTD., Dublin (IE)

( * ) Notice: Subject to any disclaimer, the term of this patent is extended or adjusted under 35 U.S.C. 154(b) by 0 days.

(21) Appl. No.: 16/663,867

(22) Filed: Oct. 25, 2019

(65) Prior Publication Data
US 2020/0054797 A1   Feb. 20, 2020

Related U.S. Application Data

(63) Continuation of application No. 15/037,995, filed as application No. PCT/EP2014/074858 on Nov. 18, 2014, now abandoned.

(30) Foreign Application Priority Data

Nov. 20, 2013   (IT) .......................... MI2013A001927

(51) Int. Cl.
*A61L 31/06*   (2006.01)
*A61K 49/00*   (2006.01)
(Continued)

(52) U.S. Cl.
CPC .............. *A61L 31/06* (2013.01); *A61B 1/018* (2013.01); *A61B 1/273* (2013.01); *A61J 1/05* (2013.01);
(Continued)

(58) Field of Classification Search
CPC ...... A61L 31/06; A61L 24/001; A61L 24/046; A61L 2400/06; A61L 2300/442;
(Continued)

(56) References Cited

U.S. PATENT DOCUMENTS 3,740,421 A   6/1973   Schmolka et al.
5,380,292 A   1/1995   Wilson
(Continued)

FOREIGN PATENT DOCUMENTS

CN   1356896 A   7/2002
CN   1753949 A   3/2006
(Continued)

OTHER PUBLICATIONS

Jeon et al. (KR20130079297A Machine Translation) hereinafter Jeon (Year: 2013).*
(Continued)

*Primary Examiner* — Aradhana Sasan
*Assistant Examiner* — Quanglong N Truong
(74) *Attorney, Agent, or Firm* — Rothwell, Figg, Ernst & Manbeck, P.C.

(57) ABSTRACT

The invention provides a pharmaceutical composition in form of emulsion or microemulsion for use in an endoscopic procedure, preferably said endoscopic procedure comprising the administration of said pharmaceutical composition to a human with the aim of improving and facilitating the resection of the lesion by raising the area where the lesion is located. The invention herein disclosed provides a method for performing an endoscopic procedure, said method preferably comprising the administration of a pharmaceutical composition in form of emulsion or microemulsion to a human.

19 Claims, 1 Drawing Sheet

(51) Int. Cl.
  *A61L 24/04*  (2006.01)
  *A61L 24/00*  (2006.01)
  *A61B 1/018*  (2006.01)
  *A61B 1/273*  (2006.01)
  *A61J 1/05*  (2006.01)
  *A61J 1/06*  (2006.01)
  *A61M 5/00*  (2006.01)
  *A61M 5/178*  (2006.01)
  *A61M 5/32*  (2006.01)
  *A61M 39/10*  (2006.01)

(52) U.S. Cl.
  CPC ............ *A61J 1/06* (2013.01); *A61K 49/006* (2013.01); *A61L 24/001* (2013.01); *A61L 24/046* (2013.01); *A61M 5/007* (2013.01); *A61M 5/178* (2013.01); *A61M 5/329* (2013.01); *A61M 39/10* (2013.01); *A61L 2300/442* (2013.01); *A61L 2400/06* (2013.01)

(58) Field of Classification Search
  CPC .... A61L 24/0005; A61L 31/14; A61M 39/10; A61M 5/178; A61M 5/007; A61M 5/329; A61K 49/006; A61K 9/0019; A61K 9/107; A61K 9/1075; A61K 47/10; A61K 47/22; A61K 9/113; A61K 49/18; A61J 1/05; A61J 1/06; A61B 1/273; A61B 1/018; A61P 41/00
  See application file for complete search history.

(56) References Cited

U.S. PATENT DOCUMENTS

| | | | |
|---|---|---|---|
| 7,909,809 | B2 | 3/2011 | Scopton et al. |
| 8,282,621 | B2 | 10/2012 | Scopton et al. |
| 8,864,738 | B2 | 10/2014 | Scopton et al. |
| 9,226,996 | B2 | 1/2016 | Moro |
| 2005/0220831 | A1 | 10/2005 | Jorsal |
| 2006/0070631 | A1 | 4/2006 | Scopton et al. |
| 2008/0181952 | A1 | 7/2008 | Vogel et al. |
| 2011/0052490 | A1 | 3/2011 | Vogel |
| 2011/0087207 | A1 | 4/2011 | Vogel et al. |
| 2012/0003283 | A1 | 1/2012 | Weiss et al. |
| 2012/0045489 | A1* | 2/2012 | Tong ............... A61K 9/0019 424/400 |

FOREIGN PATENT DOCUMENTS

| | | |
|---|---|---|
| CN | 101932287 A | 12/2010 |
| CN | 102048688 A | 5/2011 |
| CN | 102215900 A | 10/2011 |
| CN | 103386139 A | 11/2013 |
| EP | 2494957 A1 | 9/2012 |
| JP | 2003502363 A | 1/2003 |
| JP | 2011505377 A | 2/2011 |
| JP | 2013509361 A | 3/2013 |
| WO | 9318852 A1 | 9/1993 |
| WO | 0078301 A1 | 12/2000 |
| WO | 2009070793 A1 | 6/2009 |
| WO | 2011050739 A1 | 5/2011 |
| WO | 2011103245 A1 | 8/2011 |

OTHER PUBLICATIONS

International Search Report dated Dec. 10, 2014, in PCT/EP2014/074858, 3 pages.
Search Report dated Jul. 24, 2014, in IT MI20131927, 11 pages.
Fernandez-Esparrach, G., et al., "Efficacy of a reverse-phase polymer as a submucosal injection solution for EMR: A comparative study (with video)," Gastrointestinal Endoscopy, 2009, vol. 69, No. 6, pp. 1135-1139.
Jeppsson, R., et al., "The influence of emulsifying agents and of lipid soluable drugs on the fractional removal rate of lipid emulsions from the blood stream of the rabbit," Acta Pharmacol. et Toxicol., 1975, vol. 37, pp. 134-144.
Polymeros, D., et al., "Comparative performance of novel solutions for submucosal injection in porcine stomachs: An ex vivo study," Digestive and Liver Disease, 2010, vol. 42, pp. 226-229.
Uraoka, T., et al., "Submucosal injection solution for gastrointestinal tract endoscopic mucosal resection and endoscopic submucosal dissection," Drug Design, Development and Therapy, 2008, vol. 2, pp. 131-138.
Eun, S. H., et al., "Effectiveness of sodium alginate as a submucosal injection material for endscopic mucosal resection in animal," Gut and Liver, vol. 1, No. 1, 2007, pp. 27-32.
Escobar-Chavez, J. J., et al., "Applications of thermo-reversible pluronic F-127 gels in pharmaceutical formulations," J. Pharm Pharmaceutic Sci (www.cspsCanada.org), 2006, vol. 9, No. 3, pp. 339-358.
Yapar, E. A., et al., "Poly(ethylene oxide)-poly(propylene oxide)-based copolymers for transdermal drug delivery: An overview," Tropical Journal of Pharmaceutical Research, 2012, vol. 11, No. 5, pp. 855-866.
Eccleston, G. M., "Emulsions and microemulsions," Encyclopedia of Pharmaceutical Technology, 2007, Informa Healthcare USA, Inc., pp. 1548-1565.
Mayo Clinic, Clinical Update, Current Trends in the Practice of Medicine, 2011, vol. 27, No. 6, 2 pages.
Repici et al. "Standard Needle versus needless injection modality: animal study on different fluids for submucosal elevation" Gastrointestinal Endoscopy (Jan. 2017), doi: 10.2016/j.gie.2017.01.029—19 pages.
Japanese Office Action issued in Application No. 2016-533197 dated Jul. 31, 2018, with English Translation, 9 pages.
Onta, H. et al.,"Endoscopic Intramural Injection of Anti-Neoplastic Emulsion", Gann, 75 (7), Jul. 1984, pp. 641-649.
Chinese Office Action issued in Application No. 201480063652.8 dated Oct. 31, 2018, with English Translation, 16 pages.

* cited by examiner

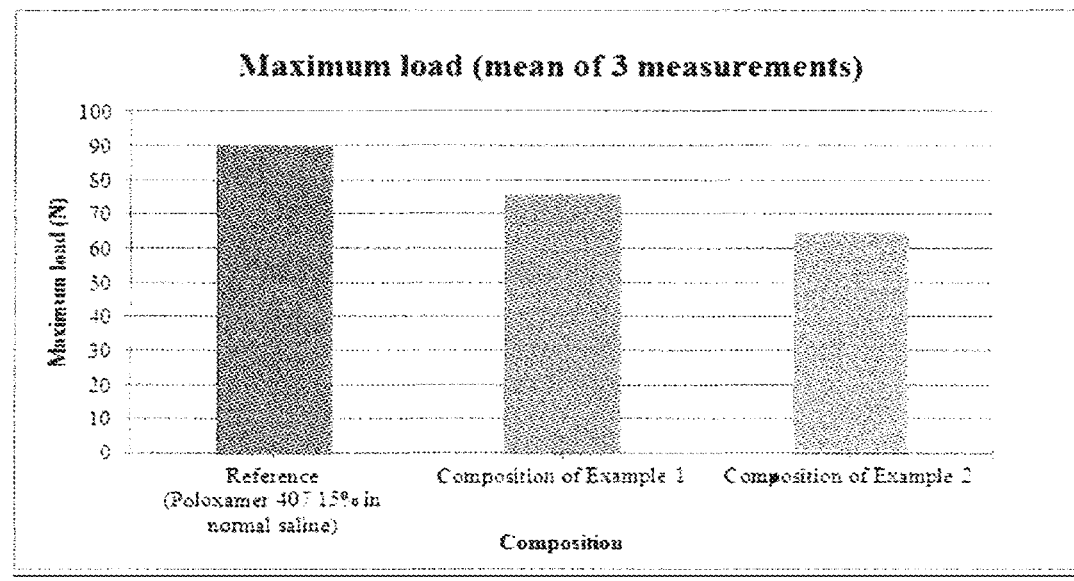

EMULSIONS OR MICROEMULSIONS FOR USE IN ENDOSCOPIC MUCOSAL RESECTIONING AND/OR ENDOSCOPIC SUBMUCOSAL DISSECTION

CROSS-REFERENCE TO RELATED APPLICATIONS

The present invention is a continuation of U.S. patent application Ser. No. 15/037,995, filed on 19 May 2016, which is a national stage filing under 35 U.S.C. § 371 of PCT/EP2014/074858, filed on 18 Nov. 2014, and claims the benefit of priority to Italian application Serial No. MI2013A001927, filed 20 Nov. 2013. Each application is incorporated herein by reference in its entirety.

FIELD OF THE INVENTION

The present invention relates to a pharmaceutical composition in form of emulsion or microemulsion and the use thereof as aid during endoscopic procedures in which it is injected in a target tissue in order to form a cushion. More in details, the invention relates to a method for performing an endoscopic procedure, which comprises injecting said pharmaceutical composition in form of emulsion or microemulsion in a target tissue of a patient, in order to form a cushion, which cushion is then optionally subjected to an endoscopic surgical procedure, such as a resection.

BACKGROUND OF THE INVENTION

Endoscopy is a diagnostic and medical procedure which allows to examine the interior of a hollow organ or cavity of the body by means of an instrument called endoscope, without employing invasive surgery. Endoscopy is commonly used for diagnostic purposes, even though minor, non-invasive surgical and non-surgical interventions can be performed during an endoscopic procedure. Typically, said minor interventions comprise cauterization of a bleeding vessel, widening a narrow esophagus, removing polyps, adenomas and small tumors, performing biopsies or removing a foreign object. Endoscopy is used by specialists to examine, for example, the gastrointestinal tract, the respiratory tract, the ear, the urinary tract, the female reproductive system and, through small incisions, normally closed body cavities such as the abdominal or pelvic cavity (laparoscopy), the interior of a joint (arthroscopy) and organs of the chest (thoracoscopy and mediastinoscopy). The endoscope is an illuminated usually optic fiber flexible or rigid tubular instrument for visualizing the interior of a hollow organ or part (as the bladder, stomach, intestine or esophagus) for diagnostic or therapeutic purposes, that typically has one or more working channels to enable passage of instruments (as forceps, electrosurgical knife, endoscopic injection needles or scissors) or to facilitate the removal of bioptic samples. It includes a suitable lamp and imaging device at its distal portion, and it can be inserted through natural occurring openings of the body, such as the mouth, the anus, the ear, the nose or through small surgical incisions. Given the wide variety of body organs or cavities which can be examined by means of endoscopic procedures, several types of endoscopes exist, such as, for example, laryngoscope, thoracoscope, angioscope, colonoscope, enteroscope, sigmoidoscope, rectoscope, proctoscope, anoscope, arthroscope, rhinoscope, laparoscope, hysteroscope, encephaloscope, nephroscope, esophagoscope, bronchoscope, gastroscope, amnioscope, cystoscope.

In particular, endoscopic procedures are widely applied in the gastrointestinal tract, both for diagnostic purposes and for small surgical interventions. With the progress advance of the imaging technology, endoscopic procedures can be used to accurately examine the mucosa that covers the gastrointestinal cavities, and to detect small and large pathological lesions, such as inflammatory tissue, polyps, pseudopolyps, serrated lesions, adenomas, ulcerations, dysplasias, pre-neoplastic and neoplastic formations, tumors and similar. In addition, endoscopic procedures in the gastrointestinal tract allow the doctor to perform minor, surgical or non-surgical interventions, which comprise, for example, biopsies and removal of pathologic lesions (polyps, adenomas, dysplasias, Barrett's dysplasia, pre-neoplastic and neoplastic formations, tumors). Surgical interventions include two endoscopic resection procedures commonly used in gastrointestinal endoscopy to remove pathological lesions are endoscopic mucosal resection (EMR) and endoscopic submucosal dissection (ESD). These two techniques have provided new alternatives for minimally invasive treatment of gastrointestinal polyps, adenomas, dyspalsias (such as Barrett's dysplasia) and early-stage cancers that involve a minimum risk of lymph-node metastasis. EMR is an endoscopic technique developed for removal of sessile or flat neoplasms confined to the superficial layers (mucosa and submucosa) of the GI tract. EMR is typically used for removal of lesions smaller than 2 cm or piecemeal removal of larger lesions. EMR also plays an important role in the assessment of resected specimens for accurate pathological staging. In contrast to polypectomy, EMR involves the lifting up of a lesion from the muscular layer by injecting a fluid agent, commonly normal saline (NS) solution, into the submucosal layer. EMR is also useful for obtaining specimens for accurate histopathological staging to determine the risk of lymph-node metastasis. EMR facilitates the complete removal of the affected mucosa by excising through the middle or deeper portion of the gut wall submucosa. Various EMR techniques have been described and four methods involving snare resection are commonly used: (1) the inject and cut method; (2) the inject, lift, and cut method; (3) cap-assisted EMR (EMRC); and (4) EMR with ligation (EMRL). The inject and cut technique, also known as submucosal injection polypectomy, has become widely used in recent years because of its simplicity. The diseased mucosa is lifted up from the muscular layer by creating a submucosal fluid cushion, captured, strangulated using an electrosurgical snare, and then resected. However, injection into the thin submucosal layer is a delicate process, the injected solution tends to dissipate quickly, flat and depressed lesions are hard to capture with the snare compared with protruded lesions, and large or awkwardly located lesions can be difficult to remove (Uraoka et al., Drug Design, Development and Therapy 2008: 2 131-138). Injection-assisted EMR is frequently used for large flat colon polyps.

Endoscopic submucosal dissection (ESD), a relatively new endoscopic resection procedure, was developed specifically for removing larger lesions. Lesions are dissected directly along the submucosal layer using an electrosurgical knife, resulting in an en-bloc resection of even large lesions. ESD has been predicted to replace conventional surgery in treating certain cancerous stages, but since it has a higher rate of perforation and bleeding complications than conventional EMR, a greater degree of endoscopic skill and experience is required than for EMR. Various submucosal injection solutions had previously been developed and shown to be satisfactory for use during EMR, but introduction of the lengthier ESD procedure requires a longer-lasting solution to help identifying the cutting line during dissection of the submucosal layer (Uraoka et al., Drug Design, Development and Therapy 2008: 2 131-138).

The use of submucosal injection is essential for a successful EMR, as injection of fluid into the submucosa cushions facilitates the isolation of the tissue to be removed just before capture of the target lesion with a snare, thereby reducing thermal injury and the risk of perforation and hemorrhage while also facilitating an en-bloc resection. Submucosal injection is considered to play an important role in the EMR procedure, and the "ideal" submucosal injection solution should be both long-lasting and capable of producing a hemispheric shape to facilitate snaring. In addition, providing a sufficiently high submucosal elevation is important for safe submucosal cutting during the ESD procedure (Uraoka et al., Drug Design, Development and Therapy 2008: 2 131-138).

The ideal solution for injection-assisted EMR should be safe, inexpensive, non toxic, readily available, easy to inject and it should be capable of providing a high, long-lasting submucosal cushion. Wound healing characteristics should be also requested to facilitate the closure of the wound created by the removal of the resected mucosa, as well as the presence of a coloring agent (such as a dye) will allow to distinguish more easily the deepness of the submucosal layer, avoiding undue perforation during ESD.

Normal saline solution (NS) has been commonly used for this purpose, but it is difficult to produce the proper submucosal fluid cushion and maintain the desired height, particularly for flat elevated lesions, because of the rapid dispersion of the solution through the mucosal layers and absorption of NS into the surrounding tissue (Uraoka et al., Drug Design, Development and Therapy 2008: 2 131-138). For this reason, in long-lasting procedures and in the removal of large lesions, such as large flat polyps, repeated injection of the solution into the submucosal layer are required, with a consequent operational complication for the personnel of the endoscopic unit.

In order to overcome the fast disappearance of the cushion, which represents a typical problem encountered with NS, during the past decade several types of solutions have been described and tested for the use in solution-assisted EMR. Each type of solution has its advantages and disadvantages. For example, hyaluronic acid (HA) solutions have been reported as the best agents for submucosal injections. HA solutions provide long-lasting fluid cushions and allow high successful en-bloc resections and low perforation complication rates. Moreover, HA is safe and non-toxic, since it is a physiological component of the extracellular matrix. The main disadvantage of HA is its high cost, which renders it quite inaccessible for most endoscopic units. Other solutions have been tested and described, such hypertonic dextrose and hydroxypropyl methylcellulose (HPMC), which however have been reported to cause tissue damage and inflammation. Another recently investigated injection solution is fibrinogen mixture (FM) solution, which has a high viscosity and produces a long-lasting submucosal elevation, thus lowering the number of injections per lesion and shortening procedure times; in addition, FM is inexpensive. The main disadvantage of FM is the possible the risk of transmission of viruses: since FM is obtained by the fractionalization of coagulation proteins in human serum, contamination with hepatitis or other viruses is possible. As above illustrated, an ideal solution for EMR and ESD has not yet been developed, and many researches in this field are still on-going.

Ideally, viscous solutions such as HA solutions or HPMC solutions could meet the requirements of the endoscopic resection procedures, since they could provide a high and long-lasting cushion because of the low tendency of the water coordinated by these polymers to diffuse and spread out in the tissues surrounding the lesion. However, the use of viscous solutions, such as HA solutions or HPMC solutions, poses some challenges in the procedure, due to the difficulty to get a viscous solution flowed through the injection devices. As a matter of facts, in gastrointestinal EMR and ESD procedures, the injections of the cushion-forming solutions are performed using endoscopic injection needles. As well known in the art, endoscopic injection needles are devices which can be long up to about 230 cm and which include a relatively long catheter within which an inner tube having a distal injection needle is slideably disposed. A proximal actuating handle is coupled to the catheter and the injection tube for moving one relative to the other when necessary. Fluid access to the injection tube is typically provided via a luer connector on the handle. Endoscopic injection needle devices are typically delivered to the injection site through the working channel of the endoscope. In order to protect the lumen of the endoscope working channel from damage, the handle of the infusion needle device is manipulated to withdraw the distal injection needle into the lumen of the catheter before inserting the device into the endoscope. This is important to prevent exposure of the sharp point of the injection needle as the device is moved through the lumen of the endoscope. When the distal end of the endoscopic injection needle device is located at the injection site, its handle is again manipulated to move the injection needle distally out of the lumen of the catheter. When advanced to the most distal position, the exposed portion of the injection needle is approximately 4-6 mm in length. After the injection site has been pierced, the solution, usually contained in a 5 mL to 10 mL syringe provided with a luer-lock fitting connected to the handle of the injection needle, is delivered through the injection tube and the needle into the injection site.

The injection needle and other accessories commonly used during endoscopic procedures, such as snares for polypectomy, clipping devices, biopsy forceps and similar, are passed through one or more specific channels of the endoscope, usually called working channels or operating channels. Depending upon the type of endoscope used in GI endoscopy (e.g. gastroscope, enteroscope, colonoscope, duodenoscope, sigmoidoscope and similar), the inner diameter of the working channels may vary considerably. However, the most common endoscopes used in GI endoscopy have working channels with inner diameter in the range from about 2 mm to about 5 mm. Generally, the manufacturers of endoscopic accessories produce accessories having outer diameters which allow them to fit all the working channels. In particular, as regards the endoscopic injection needles, the outer diameter of catheter ranges from 1.9 trim to 2.3 mm; thus, considering that the inner injection tube is contained in the outer catheter, its internal diameter is usually 1 mm or less. Such a small diameter of the injection tube causes a high dynamic resistance to the flowing of the solution; this is more valid and important when a viscous solution is used. For this reason, the viscous solutions used for EMRs and ESDs often need to be diluted before their use to make the solutions able to flow through the injection needle, with a loss of their characteristics of providing a high and long-lasting cushion. To obviate to this problem, WO2011/103245 A1 describes a kit and a method for delivering a injectable solution to a tissue treatment site, for use in ESD. Said kit includes a housing having a chamber, a proximal portion and a distal portion. An injectable solution having a viscosity greater than about 10000 cP is provided in the chamber. The kit also includes a plunger movably positionable within the proximal portion of the chamber, the plunger provides a seal at the proximal end portion. A pressure gauge is also provided with the kit. A handle is connected to the housing and a plunger advancing member having a plunger handle is connected thereto. The plunger advancing member is provided separate from the housing and includes a distal portion configured for operably connecting with the proximal portion of the housing. The kit also includes an inner shaft provided separate from the housing and having a proximal end portion configured for operably connecting with the distal portion of the housing for receiving the injectable solution there through and a distal end configured for insertion in to the tissue treatment site. As a skilled in the art would recognize, such a device allows the physician to apply a pressure much higher than using a normal syringe, thus allowing the high viscous solution, having a viscosity of 10000 cP or greater, to flow into the injection tube. Furthermore, WO2011/103245 A1 discloses that suitable materials for inclusion in the injectable solution include methylcelluloses, such as carboxymethyl cellulose (CMC) and hydroxypropyl methylcellulose (HPMC), extracellular matrix proteins, elastin, collagen, gelatin, fibrin, agarose, and alginate or mixtures thereof. However, the use of such a "high-pressure" generating device during the endoscopic examination is known for being not favorably accepted by the experts of the field, since it is cumbersome, additional work is required to put it in place, it is difficult to be operated and therefore it represents a complication of the EMR and ESD procedures.

Another tentative to overcome these issues is described in WO2009/070793 A1, which discloses the use of purified inverse thermosensitive polymers in EMR. As well known in the art, inverse thermosensitive polymers are polymers which, upon dissolution in solvents (such as water) in a concentration above the critical micellar concentration (CMC), provide solutions that show inverse characteristics of viscosity, which means that said solutions display an increase of their viscosity with the temperature. In particular, solutions of said polymers form gels above the CGC (critical gelation concentration), when the temperature is raised above the CGT (critical gelation temperature). The gelation is due to physical entanglement and packing of the micellar structures, and it is reversible, thus the gel turns back to a liquid form when temperature is lowered below the critical gelation temperature. Polymers of this kind are well known in the art, and comprise, for examples, poloxamers (commercialized by BASF under the brand name of Kolliphor™) and poloxamines (commercialized by BASF under the brand name of Tetronic™). Aqueous solutions of those polymers at concentrations above CGC can be liquid at room temperature and can form a gel once heated up to body temperature (i.e. about 37° C.). WO2009/070793 A1 discloses the use of a composition comprising a purified inverse thermosensitive polymer in an endoscopic procedure for gastrointestinal mucosal resectioning. Said composition, called. LeGoo-endo™, is an aqueous solution of purified poloxamer 237; it is disclosed that the rapid reversible liquid to gel transition achieved as a result its purified nature allows LeGoo-endo™ to be liquid at room temperature and to become a gel only as it emerges from the catheter at the EMR site, once heated to body temperature. WO2009/070793 A1 teaches that, in order to obtain said rapid liquid to gel transition, the use of a purified poloxamer was needed, and that said purified poloxamer was obtained by a purification process aimed to the obtainment of a purified polymer characterized by a lower polydispersity of the molecular weight. Moreover, WO 2009/070793 A1 discloses that it was necessary to develop a method of injecting through a catheter into the intestine or stomach a purified inverse thermosensitive polymer solution that transitions to a gel at body temperature. Among the challenges overcome was the fact that because the catheter quickly reaches body temperature while resident inside the body, the purified inverse thermosensitive polymer could gel inside the catheter prior to reaching the desired site for EMR. WO2009/070793 A1 teaches that the delivery problems were solved with a system comprising a high-pressure needle catheter connected to a syringe filled with purified inverse thermosensitive polymer solution, wherein said high-pressure needle catheter was contained within an administration device (e.g., a syringe pump) that generated pressure on the plunger of the syringe through a manual (e.g., screw), electrical or pressurized-gas mechanism. As a matter of facts, in the in vivo example, WO2009/070793 A1 discloses that five EMR were performed in the colon of 2 pigs with LeGoo-endo™ using a 23-gauge scletotherapy needle with a 5-mL syringe and a balloon dilator gun; LeGoo-endo™ was kept on ice during the intervention. Saline containing syringes were also kept on ice to cool the catheter immediately before poloxamer injections. As a person skilled in the art will recognize, the operating procedure disclosed by WO2009/070793 A1 is quite complex, for the following reasons: it requires the use of a particular, high-pressure needle catheter; it requires an administration device (e.g., a syringe pump) that generates pressure on the plunger of the syringe to administer the purified inverse thermosensitive polymer solution.

U.S. Pat. No. 7,909,809 teaches a method for performing an interventional endoscopic procedure in the gastrointestinal tract such as polipectomy, endoscopic mucosal resection (EMR) and endoscopic submucosal dissection (ESD), said method comprising the administration to a human of a bulking or cushioning material that has characteristics of phase transition from a low viscosity state (e.g. liquid phase) into a high viscosity state (e.g. gel phase) in response to a predetermined temperature (e.g. body temperature).

As delineated above, an ideal composition for endoscopic mucosal resection (EMR) and for endoscopic submucosal dissection (ESD) has not yet been developed. HA (hyaluronic acid) provides viscous solutions capable of providing long-lasting submucosal cushions and is safe and non toxic, but it is known to be highly expensive.

Cellulose derivatives, such as HPMC and CMC, are cheap and their solutions are capable of providing long-lasting submucosal cushions; however, due to their viscosity, a particular device such a syringe pump is required to make them flow into the injection needle, thus they are known for being difficult and uncomfortable to be injected.

Inverse thermosensitive polymers, such as poloxamers and poloxamines, are cheap and their solutions, thanks to their capability of gelling at body temperature, are capable of providing long-lasting submucosal cushions; it is however known in the art that, to obtain the desired effect, such polymers need to be contained in the solution in a concentration equal to or above the critical gelation concentration (CGC), i.e. above the concentration at which the transition of phase from solution to gel occurs. Accordingly, such polymers are usually contained in the known solutions in an amount equal to or above 15% by weight, with respect to the weight of the composition (namely, above the CGC); thus the viscosity of said solutions is too high to allow them to be manually injected, and the use of a syringe pump is needed, with an evident disadvantage for the endoscopist. Therefore, there is the need for a composition for use in endoscopic resection procedures which is effective in providing a high, long-lasting submucosal cushion and in the meantime is manually injectable through the endoscopic injection needle, without the need of using a high-pressure generating administration device, such as a syringe pump.

BRIEF DESCRIPTION OF THE FIGURE

FIG. 1 Maximum load (expressed in Newton) of the compositions according to Examples 1 and 2 in comparison with the Reference solution.

SUMMARY OF THE INVENTION

The invention herein disclosed provides a pharmaceutical composition in form of emulsion or microemulsion and the use thereof in endoscopic procedures, preferably gastrointestinal endoscopic procedures.

The invention herein disclosed provides a pharmaceutical composition in form of emulsion or microemulsion for use in an endoscopic procedure, wherein said pharmaceutical composition in form of emulsion or microemulsion comprises at least one inverse thermosensitive polymer and at least one physiologically acceptable excipient.

Said endoscopic procedure is preferably an endoscopic resection of the mucosa performed during a gastrointestinal endoscopy, more preferably a polypectomy, an endoscopic mucosal resection (EMR) and/or an endoscopic submucosal dissection (ESD).

According to the invention, said gastrointestinal endoscopy is preferably performed in the esophagous, stomach and/or small intestine (duodenum, jejunum, ileum), in the cecum, in the colon, in the sigmoid colon and/or in the rectum.

The invention herein disclosed provides a method for performing an endoscopic procedure, said method comprising the administration of a pharmaceutical composition in form of emulsion or microemulsion to a human, wherein said pharmaceutical composition in form of emulsion or microemulsion comprises at least one inverse thermosensitive polymer and at least one physiologically acceptable excipient. According to the invention, said endoscopic procedure is preferably an endoscopic resection of the mucosa performed during a gastrointestinal endoscopy, more preferably a polypectomy, an endoscopic mucosal resection (EMR) and/or an endoscopic submucosal dissection (ESD).

Said gastrointestinal endoscopy is preferably performed in the esophagous, stomach and/or small intestine (duodenum, jejunum, ileum), in the cecum, in the colon, in the sigmoid colon and/or in the rectum.

Further, the invention herein disclosed provides a kit for use in an endoscopic procedure, said kit comprising a pharmaceutical composition in form of emulsion or microemulsion, an endoscopic injection needle, a syringe and instruction for use thereof, wherein said pharmaceutical composition in form of emulsion or microemulsion comprises at least one inverse thermosensitive polymer and wherein said endoscopic procedure is preferably an endoscopic resection of the mucosa performed during a gastrointestinal endoscopy, more preferably a polypectomy, an endoscopic mucosal resection (EMR) and/or an endoscopic submucosal dissection (ESD).

More in details, the pharmaceutical composition in form of emulsion or microemulsion is injected in a target tissue in order to form a cushion, which may be then optionally subjected to an endoscopic surgical procedure, such as a resection.

All publications, patents and patent applications cited herein, whether supra or infra are hereby incorporated by reference in their entirety.

DETAILED DESCRIPTION OF THE INVENTION

The inventors have been working to find out innovative pharmaceutical compositions for use in endoscopic procedures, preferably endoscopic mucosal resection (EMR) and/or endoscopic submucosal dissection (ESD), embodying the characteristics requested by endoscopic physicians, said characteristics being preferably safety, inexpensiveness, absence of toxic effects, easiness to be injected and capacity of providing a high, long-lasting submucosal cushion. In particular, many efforts were made in order to find a composition effective in providing a high, long-lasting submucosal cushion characterized by an improved flowability, and thus by a reduced resistance to injection through the endoscopic injection needles commonly used in the endoscopic procedures than the compositions known in the art.

It was surprisingly discovered that pharmaceutical compositions in form of emulsions or microemulsions comprising at least one inverse thermosensitive polymer and optionally at least one physiologically acceptable excipient have an improved flowability than similar compositions formulated as simple aqueous solutions. Accordingly, it was discovered that the resistance to the injection obtained with the pharmaceutical compositions in form of emulsions or microemulsions according to the invention herein disclosed, comprising at least one inverse thermosensitive polymer and at least one physiologically acceptable excipient, is lower than the resistance to the injection of similar compositions formulated as simple aqueous solutions. The tests of flowability and of resistance to injection were performed in the laboratory under the same test conditions and using the same endoscopic injection needles. As a matter of facts, similar compositions containing at least one inverse thermosensitive polymer and the same auxiliary components were formulated in both forms, namely as the simple aqueous solutions known in the art and according to the emulsions or microemulsions of the invention. It was surprisingly discovered that formulating said compositions in form of emulsions or microemulsions according to the invention leads to the obtainment of final compositions which have a better flowability through the endoscopic injection system, (preferably, composed by a catheter and a retractable needle) than the corresponding compositions formulated in form of simple aqueous solutions. Therefore, it was discovered that the pharmaceutical compositions in form of emulsions or microemulsions according to the invention herein disclosed, comprising at least one inverse thermosensitive polymer and optionally at least one physiologically acceptable excipient, have the notable advantage to be easily injectable which means that the endoscopist can inject them with a minor effort than the corresponding compositions formulated in form of simple aqueous solution. Accordingly, the administration of the pharmaceutical compositions in form of emulsion or microemulsion according to the invention herein disclosed does not require the use of a special administration device (e.g., a syringe pump) that generates a high pressure on the plunger of the syringe, since the injection through the endoscopic injection needle can be manually and more easily performed.

Moreover, it was discovered that, formulating the pharmaceutical compositions in form of emulsions or microemulsions rather than simple aqueous solutions does not affect their capability of gelling upon heating, characteristic that could be particularly useful due to the temperature gap between the typical room temperature (e.g. about 20-25° C.) and the body temperature (e.g. about 37° C.). As well known in the art, inverse thermosensitive polymers are polymers which, upon dissolution in water in suitable ranges of concentration, i.e. above the critical gelation concentration (CGC), provide solutions that show inverse characteristics of viscosity, which means that said solutions display an increase of their viscosity with the temperature. In particular, aqueous solutions of said polymers form hydrogels above the critical gelation concentration (CGC), when the temperature is raised above the critical gelation temperature (CGT). The gelation is due to physical entanglement and packing of the micellar structures, and it is reversible, thus the gel turns back to a liquid form when temperature is lowered below the critical gelation temperature. It was here discovered that pharmaceutical compositions in form of emulsions or microemulsions according to the invention herein disclosed, comprising at least one inverse thermosensitive polymer, have the same gelling properties of similar compositions formulated as simple aqueous solutions. Accordingly, it was discovered that the pharmaceutical compositions in form of emulsions or microemulsions according to the invention herein disclosed, comprising at least one inverse thermosensitive polymer, have the same thermosensitive behaviour of similar compositions formulated as simple aqueous solutions which means that both said compositions in form of emulsions or microemulsions of the invention and said compositions formulated as simple known aqueous solutions are liquid at room temperature (i.e. about 20° C.-25° C.) and become gels upon heating at body temperature (i.e. about 37° C.) if said at least one inverse thermosensitive polymer contained in the emulsion or microemulsion of the invention is within the suitable concentration range.

The invention herein disclosed provides a pharmaceutical composition in form of emulsion or microemulsion and the use thereof in endoscopic procedures, preferably gastrointestinal endoscopic procedures.

The invention herein disclosed provides a pharmaceutical composition in form of emulsion or microemulsion for use in an endoscopic procedure, wherein said pharmaceutical composition in form of emulsion or microemulsion comprises at least one inverse thermosensitive polymer and optionally at least one physiologically acceptable excipient.

Preferably, said endoscopic procedure comprises the administration of said pharmaceutical composition to a human to enhance the easiness of lesion removal or polyps and/or adenoma and/or cancer dissection from the mucosal surface by creating a raised cushion in the mucosal surface interested to the lesion removal.

The invention herein disclosed provides also a method for performing an endoscopic procedure, preferably said method comprising the administration of a pharmaceutical composition in form of emulsion or microemulsion to a human, wherein said pharmaceutical composition in form of emulsion or microemulsion comprises at least one inverse thermosensitive polymer. More in details, the pharmaceutical composition is injected in a target tissue of said human in order to form a cushion which is then optionally subjected to an endoscopic surgical procedure, such as a resection. In another aspect, the invention herein disclosed provides a kit for use in an endoscopic procedure, said kit comprising a pharmaceutical composition in form of emulsion or microemulsion, an endoscopic injection needle, a syringe and instructions for use thereof. The use of such a kit is particularly useful when the at least one inverse thermosensitive polymers is contained in the composition in an amount equal to or above the CGC (critical gelation concentration).

According to a preferred embodiment, said endoscopic procedure is an endoscopic resection procedure performed during a gastrointestinal endoscopy. According to an embodiment, said endoscopic resection procedure is polypectomy. According to another embodiment, said endoscopic resection procedure is endoscopic mucosal resection (EMR). According to further another embodiment, said endoscopic resection procedure is endoscopic submucosal dissection (ESD).

Said gastrointestinal endoscopy is preferably performed in the esophagous, stomach and/or small intestine (duodenum, jejunum, ileum), in the cecum, in the colon, in the sigmoid colon and/or in the rectum.

According to the invention said polypectomy, endoscopic mucosal resection (EMR) and/or said endoscopic submucosal dissection (ESD) are used for the removal of mucosal lesions, polyps, pseudo-polyps, flat polyps, adenomas, serrated lesions, dyspalsias, Barrett's dysplasia, pre-neoplastic and neoplastic formations, tumors during gastrointestinal endoscopy.

According to an embodiment, said pharmaceutical composition in form of emulsion or microemulsion is administered to a human through injection to enhance the easiness of removing lesions, such as polyps and/or adenoma and/or cancers, from the mucosal surface by creating a raised cushion in the mucosal surface affected by the pathological lesion.

According to the invention, said polypectomy, endoscopic mucosal resection (EMR) and/or said endoscopic submucosal dissection (ESD) are also used for the removal of pathologic and/or dysplastic mucosal tissue in case of esophagitis, erosive esophagitis, Barrett's esophagous (such as in ablation procedures), and/or gastrointestinal pathological hypersecretory conditions, such as Zollinger Ellison Syndrome.

According to the invention, said pharmaceutical composition in form of emulsion or microemulsion can be a water-in-oil emulsion or microemulstion, or a oil-in-water emulsion or microemulsion. According to a preferred embodiment, the pharmaceutical composition in form of emulsion or microemulsion is an oil-in-water emulsion or microemulsion.

According to an embodiment, said pharmaceutical composition in form of emulsion or microemulsion for use in an endoscopic procedure comprises:
(a) an aqueous phase;
(b) an oily phase;
(c) at least one surfactant;
(d) at least one inverse thermosensitive polymer;
(e) optionally at least one physiologically acceptable excipients.

According to another embodiment, said pharmaceutical composition in form of emulsion or microemulsion for use in an endoscopic procedure comprises:
(a) an aqueous phase;
(b) an oily phase;
(c) at least one surfactant;
(d) at least one inverse thermosensitive polymer;
(e) optionally at least one co-surfactant;
(f) optionally at least one physiologically acceptable excipients.

According to another embodiment, said pharmaceutical composition in form of emulsion or microemulsion for use in an endoscopic procedure comprises:
(a) an aqueous phase;
(b) an oily phase;
(c) at least one surfactant;
(d) at least one inverse thermosensitive polymer;
(e) optionally at least one co-surfactant;
(f) at least one dye;
(g) optionally at least one physiologically acceptable excipients.

According to another embodiment, said pharmaceutical composition in form of emulsion or microemulsion for use in an endoscopic procedure comprises:
(a) an aqueous phase;
(b) an oily phase;
(c) at least one surfactant;
(d) at least one inverse thermosensitive polymer;
(e) optionally at least one co-surfactant;
(f) at least one dye;
(g) optionally at least one agent characterized by trophic activity on the epithelial cells of the gastrointestinal mucosa;
(h) optionally at least one physiologically acceptable excipients.

According to another embodiment, said pharmaceutical composition in form of emulsion or microemulsion for use in an endoscopic procedure comprises:
(a) an aqueous phase;
(b) an oily phase;
(c) at least one surfactant;
(d) at least one inverse thermosensitive polymer;
(e) optionally at least one co-surfactant;
(f) at least one dye;
(g) optionally at least one agent characterized by having a trophic activity on the epithelial cells of the gastrointestinal mucosa;
(h) optionally at least one therapeutic agent;
(i) optionally at least one physiologically acceptable excipients.

According to another embodiment, the present invention relates to a pharmaceutical composition in form of emulsion or microemulsion which comprises, consists or essentially consists of:
(a) an aqueous phase;
(b) an oily phase;
(c) at least one surfactant;
(d) at least one inverse thermosensitive polymer;
(e) optionally at least one co-surfactant;
(f) optionally at least one dye;
(g) optionally at least one agent characterized by having a trophic activity on the epithelial cells of the gastrointestinal mucosa;
(h) optionally at least one therapeutic agent;
(i) optionally at least one physiologically acceptable excipient.

According to the invention herein disclosed, the main component of the aqueous phase of said pharmaceutical composition is water for injection. As well known in the art, water for injection represents a highly purified, distilled water, free of salts and of carbon contaminants, and free of microorganisms and of bacterial endotoxins. Water for injection is water purified by distillation or a purification process that is equivalent or superior to distillation in the removal of chemicals and of microorganisms. In some embodiments of the invention herein disclosed, said aqueous phase may comprise, in dissolved form, one or more inorganic salts selected form the group comprising, but not limited to: chlorides, bromides, iodides, phosphates, carbonates, bicarbonates, sulfates, nitrates and the like. In some embodiments, said aqueous phase may comprise, in dissolved form, one or more organic salts selected form the group comprising, but not limited to: citrates, maleates, fumarates, acetates, lactates and the like. Any mixture of the above inorganic and organic salts may be used to form the appropriate pharmaceutical composition, generally to buffer the pH of the composition in suitable biocompatible ranges or to reach the osmotic pressure required by the biologic environment where it is injected. In some embodiments, the aqueous phase of the pharmaceutical composition herein disclosed may comprise an amount of one or more inorganic and/or organic salts or mixtures thereof such as to have a final pharmaceutical composition which is hypotonic. In some embodiments, the aqueous phase of the pharmaceutical composition herein disclosed may comprise an amount of one or more inorganic and/or organic salts or mixtures thereof such as to have a final pharmaceutical composition which is isotonic. In some embodiments, the aqueous phase of the pharmaceutical composition herein disclosed may comprise an amount of one or more inorganic and/or organic salts or mixtures thereof such as to have a final pharmaceutical composition which is hypertonic. According to the invention herein disclosed, said inorganic and/or organic salts or mixtures thereof may be present in an amount ranging from 0% to 5% by weight with respect to the weight of the aqueous phase, more preferably from 0.1% to 4% by weight with respect to the weight of the aqueous phase, much more preferably from 0.5% to 3% by weight with respect to the weight of the aqueous phase. In a preferred embodiment, the aqueous phase of said pharmaceutical composition contains sodium chloride dissolved. According to the latter embodiment, said sodium chloride is present in an amount ranging from 0% to 5% by weight with respect to the weight of the aqueous phase, more preferably from 0.1% to 3% by weight with respect to the weight of the aqueous phase, much more preferably from 0.5% to 2% by weight with respect to the weight of the aqueous phase.

In some embodiments, the aqueous phase of the pharmaceutical composition herein disclosed comprises a buffer. In some embodiments, said buffer is a phosphate buffer. In some embodiments, said buffer is a citrate buffer. In some embodiments, said buffer is a bicarbonate buffer. In a preferred embodiment, said buffer is a phosphate buffer added with one or more inorganic salts unable to buffer the pH. According to the latter embodiment, the concentration of said phosphate buffer and said inorganic salts unable to buffer the pH is such as to have an aqueous phase which is phosphate buffered saline (PBS). As well known in the art, PBS is a water-based salt solution containing sodium chloride, sodium phosphate, and, optionally, potassium chloride and potassium phosphate; PBS for medical applications is an isotonic solution, i.e. its osmolarity and its pH match those of the human body. Several compositions and preparation methods of PBS are well known in the art.

According to the invention herein disclosed, the pH value of the pharmaceutical composition ranges from about 4.0 to about 9.0, more preferably from about 5.0 to about 8.0, much more preferably from about 5.5 to about 7.5. According to the invention, the pH value of said pharmaceutical composition in form of emulsion or microemulsion may be adjusted within the desired range by common techniques well known in the art, such as, for example, the addition of physiologically acceptable bases and/or acids.

According to the invention herein disclosed, said oily phase comprises at least one lipophilic compound. In some embodiments, said at least one lipophilic compound may be selected in the group of natural oils, comprising, but not limited to: almond oil, canola oil, castor oil, corn oil, cottonseed oil, olive oil, safflower oil, sesame oil, soybean oil and the like. In some embodiments, said at least one lipophilic compound may be selected in the group of fatty acid esters, comprising, but not limited to: isopropyl palmitate, isopropyl myristate, ethyl oleate and the like. In some embodiments, said at least one lipophilic compound may be selected in the group of fatty alcohols, comprising, but not limited to: myristic alcohol, oleyl alcohol and the like. In some embodiments, said at least one lipophilic compound may be selected in the group of fatty acids, comprising, but not limited to: myristic acid, oleyl acid, palmitic acid and the like. In some embodiments, said at least one lipophilic compound may be selected in the group of triglycerides, such as long and/or medium-chain triglycerides and the like. In some embodiments, said at least one lipophilic compound may be selected in the group of diglycerides. In some embodiments, said at least one lipophilic compound may be selected in the group of monoglycerides. Any mixture of the above lipophilic compounds can be used to form the appropriate pharmaceutical composition. In an embodiment, the lipophilic compound of said oily phase is sesame oil. In another embodiment, the lipophilic compound of said oily phase is almond oil. In another embodiment, the lipophilic compounds of said oily phase are medium-chain triglycerides. In a preferred embodiment, the lipophilic compound of said oily phase is soybean oil.

According to the invention herein disclosed, the oily phase of said pharmaceutical composition ranges from about 0.001% to about 20% by weight of the pharmaceutical composition, preferably from about 0.01% to about 2% by weight of the pharmaceutical composition, more preferably from about 0.02% to about 1% by weight of the pharmaceutical composition.

According to a preferred embodiment, said oily phase is contained in the composition of the invention in an amount from about 0.01% by weight to about 0.5% by weight, with respect to the weight of the composition.

More preferably, the oily phase is contained in the composition of the invention in an amount of about 0.08% by weight or about 0.16% by weight, with respect to the weight of the composition. Much more preferably, said oily phase is contained in the composition of the invention in an amount of about 0.02% w/w or about 0.05% w/w or about 0.1% by weight, with respect to the weight of the composition.

According to the invention herein disclosed, the pharmaceutical composition in form of emulsion or microemulsion contains at least one inverse thermosensitive polymer. According to an embodiment, said at least one inverse thermosensitive polymer is comprised at a concentration equal to or above the critical gelation concentration (CGC). According to this embodiment, said pharmaceutical composition in form of emulsion or microemulsion is characterized by a critical gelation temperature (CGT), i.e. a temperature at which the transition from a liquid state to a gel state occurs.

According to another embodiment, said at least one inverse thermosensitive polymer is comprised at a concentration below the critical gelation concentration (CGC).

The gel-forming ability of solutions of inverse thermosensitive polymers requires that the concentration of said polymers in said solutions is equal to or above the critical gelation concentration (CGC): solutions of said polymers form gels above the critical gelation concentration (CGC), when the temperature is raised above the critical gelation temperature (CGT). The critical gelation temperature (CGT) can be modulated by varying the concentration of the inverse thermosensitive polymer, which means that the higher the concentration of said polymer, the lower the critical gelation temperature (CGT). The type of inverse thermosensitive polymer used in the preparation of said composition as well as its concentration have an impact on the CGT. In the preparation of pharmaceutical compositions in form of emulsion or microemulsion according to the invention herein disclosed, the choice of the suitable inverse thermosensitive polymers and of their concentration may be made to obtain a final composition which is in liquid state below the body temperature (i.e. below about 37° C.) and which becomes a gel once heated at or above the body temperature (i.e. at or above about 37° C.). Thanks to the good flowability properties of the pharmaceutical composition in form of emulsion or microemulsion according to the invention herein disclosed, said composition can be manually and easily injected through the endoscopic injection needle into the submucosal layer of the gastrointestinal tract. Once the composition is injected into the submucosal site within the body, it is automatically heated to body temperature (i.e. about 37° C.), thus transitioning from liquid to gel form with a huge increase of its viscosity. The rapid formation of the gel inside the submucosal layer, which occurs when the concentration of the thermosensitive polymer is equal to or above the critical gelation concentration (CGC), produces a long-lasting cushion, which lasts for a time sufficient for the endoscopic resection procedure to be completed: thus, the endoscopist can easily perform the resection of the mucosal lesion found during the endoscopic examination even if the lesion is flat and not protruding into the intestinal or gastric lumen.

According to the invention herein disclosed, said at least one inverse thermosensitive polymer may be selected in the group comprising, but not limited to: polyoxyethylene-polyoxypropylene block copolymers, such as poloxamer 124, poloxamer 188, poloxamer 237, poloxamer 338, poloxamer 407 and the like. Any mixture of the above inverse thermosensitive polymers can be used to form the appropriate pharmaceutical composition. In a preferred embodiment, the inverse thermosensitive polymer of said pharmaceutical composition is poloxamer 188. In another preferred embodiment, the inverse thermosensitive polymer of said pharmaceutical composition is poloxamer 407. Further in another preferred embodiment, said inverse thermosensitive polymer comprises a mixtures of poloxamer 188 and poloxamer 407.

According to the invention herein disclosed, the amount of said inverse thermosensitive polymer ranges between about 2% to about 30% by weight with respect to the weight of the pharmaceutical composition, more preferably between about 5% to about 25% by weight with respect to the weight of the pharmaceutical composition, much more preferably between about 8% and about 20% by weight with respect to the weight of the pharmaceutical composition.

According to an embodiment, said at least one inverse thermosensitive polymers is contained in an amount equal to or above the CGC (critical gelation concentration). According to such an embodiment, the concentration of said at least one inverse thermosensitive polymer is equal to or above 15% by weight with respect to the weight of the pharmaceutical composition.

According to such an embodiment, the concentration of said at least one inverse thermosensitive polymer is selected to have the critical gelation temperature (CGT) higher than the room temperature (i.e. higher than about 20°-25° C.), preferably close to the body temperature (i.e. about 37° C.). According to the above embodiment, a preferred critical gelation temperature (CGT) of said pharmaceutical composition in form of emulsion or microemulsion is below 45° C., preferably between 10° C. and 43° C., more preferably between 20° C. and 40° C.

According to another embodiment, said at least one inverse thermosensitive polymers is contained in an amount below the CGC (critical gelation concentration). According to such an embodiment, the pharmaceutical composition in form of emulsion or microemulsion is in liquid phase up to a temperature of about 40° C. in laboratory test conditions, preferably both at room temperature (i.e. about 20-25° C.) and at body temperature (i.e. about 37° C.) in laboratory test conditions. According to the above embodiment, said pharmaceutical composition in form of emulsion or microemulsion is not able to transition from a liquid phase to a gel phase in response to the raise in temperature up to 40° C., such as from room temperature (i.e. about 20-25° C.) to body temperature (i.e. about 37° C.).

According to the invention herein disclosed, said at least one surfactant may be selected in the group of the non-ionic surfactants, comprising, but not limited to: PEG-fatty acid monoesters surfactants, such as PEG-15 hydroxystearate, PEG-30 stearate, PEG-40 laurate, PEG-40 oleate and the like; PEG-fatty acid diesters surfactants, such as PEG-32 dioleate, PEG-400 dioleate and the like; polyoxyethylene sorbitan fatty acid esters, such as polysorbate 20, polysorbate 60, polysorbate 80 and the like; polyoxyethylene alkyl ethers, such as PEG-20 cetostearyl ether, polyoxyl 25 cetostearyl, cetomacrogol 1000 and the like; sorbitan fatty acid esters surfactants, such as sorbitan monolaurate, sorbitan monopalmitate, sorbitan monooleate, and the like; propylene glycol esters of fatty acids; polyglycerol esters of fatty acids; polyoxyethylene castor oil derivatives such as polyoxyl 5 castor oil, polyoxyl 15 castor oil, polyoxyl 35 castor oil, polyoxyl 40 hydrogenated castor oil and the like; caprylocapryl polyoxyil-8 glicerides; polyoxylglycerides such as caprylocaproyl polyoxylglycerides, lauroyl polyoxylglycerides, oleoyl polyoxylglycerides and the like ceteareth 16, ceteareth 20, stearaeth 10, steareth 20, ceteth 20 and the like. Any mixture of the above non-ionic surfactant can be used to form the appropriate pharmaceutical composition. In one embodiment, the non-ionic surfactant is polysorbate 80. In a preferred embodiment, the non-ionic surfactant is PEG-15 hydroxystearate (also known as polyoxyl-15-hydroxystearate).

According to the invention herein disclosed, said at least one surfactant may be selected in the group of the ionic surfactants, comprising, but not limited to: egg lecithin, hydrogenated phosphatidyl choline from egg lecithin, soybean lecithin, hydrogenated soybean lecithin, glycerophosphocholine, soybean lysolecithin, phospholipids, hydrogenated phospholipids, sodium lauryl sulphate and the like. Any mixture of the above ionic surfactant can be used to form the appropriate pharmaceutical composition. The above ionic surfactants are commercialized by Lipoid®, under the brand-name of Lipoid®. In one embodiment, the ionic surfactant is egg lecithin. In another embodiment, the ionic surfactant is hydrogenated phosphatidyl choline from egg lecithin. In another embodiment, the ionic surfactant is soybean lecithin. Further in another embodiment, the ionic surfactant is hydrogenated soybean lecithin.

According to the invention herein disclosed, said at least one surfactant is contained in an amount which ranges from about 0.001% to about 10% by weight with respect to the weight of the pharmaceutical composition, preferably from about 0.005% to about 5% by weight with respect to the weight of the pharmaceutical composition, more preferably from about 0.01% to about 2% by weight with respect to the weight of the pharmaceutical composition.

According to a preferred embodiment, said at least one surfactant is contained in an amount of about 0.08% or about 0.1% or about 0.5% or about 0.6%, by weight with respect to the weight of the pharmaceutical composition.

The pharmaceutical composition of the invention herein disclosed may comprise at least one co-surfactant. The addition of at least one co-surfactant to the mixture oily phase-surfactant-aqueous phase is advantageous since the co-surfactant acts in synergy with the surfactant in lowering the interfacial tension of the droplets of the dispersed phase of the emulsion or microemulsion, with a stabilizing effect on the system. In the preparation of pharmaceutical compositions in form of emulsions or microemulsions according to the invention herein disclosed, said at least one co-surfactant can be selected in the groups comprising, but not limited to: low and medium chain alcohols, such as ethanol, propanol, isopropanol and the like; glycols, such as propylene glycol and the like; polyethylene glycols, such as PEG 200, PEG 300, PEG 400 and the like; DMSO; long chain alcohols, such as cetyl alcohol, myristyl alcohol, oleyl alcohol and the like; glycerol; low chain esters, such as ethyl acetate, ethyl lactate and the like; fatty acid esters, such as ethyl oleate, isopropyl myristate, isopropyl palmitate and the like; fatty acids, such as oleic acid, myristic acid and the like; salts of fatty acids, such as sodium oleate, sodium palmitate, sodium stearate and the like. Any mixture of the above co-surfactants can be used to form the appropriate pharmaceutical composition. In one embodiment, the co-surfactant is propylene glycol. In another embodiment, the co-surfactant is glycerol. In another embodiment, the co-surfactant is sodium oleate. In a preferred embodiment, the co-surfactant is a mixture of glycerol and sodium oleate.

According to the invention herein disclosed, said at least one co-surfactant is contained in an amount which ranges from about 0.00001% to about 1% by weight with respect to the weight of the pharmaceutical composition, preferably from about 0.00005% to about 0.05% by weight with respect to the weight of the pharmaceutical composition, more preferably from about 0.0001% to about 0.01% by weight with respect to the weight of the pharmaceutical composition.

The pharmaceutical composition of the invention herein disclosed may comprise at least one dye. Dyes are widely used in compositions for endoscopic procedures. In particular, in compositions for EMR and ESD procedures, the dyes are useful to feature the margins of the lesion to be resected and the physiological structures underlying the mucosa; thus, the endoscopist can easily visualize the lesion he has to remove and he can perform the procedure with less risks of damaging the submucosal layer or the muscular tissue. The dye has the function to render immediately visible to the endoscopist the submucosal layer, so that the surgical procedure is safer and there is a lower risk of damaging the structures beneath the mucosa, such as the submucosal layer itself and the external mucosal wall.

In the preparation of the pharmaceutical composition according to the invention herein disclosed, said at least one dye may be selected among vital dyes (or absorptive dyes), non-vital dyes (or contrast dyes), and reactive dyes. Vital (or absorptive) dyes, such as Lugol's solution and methylene blue, identify specific epithelial cell types by preferential absorption or diffusion across the cell membrane; non-vital (or contrast) dyes, such as indigo carmine, seep through mucosal crevices and highlight surface topography and mucosal irregularities; reactive dyes, such as congo red and phenol red, undergo chemical reactions with specific cellular constituents, resulting in a color change akin to a pH indicator. According to the invention herein disclosed, said vital (or absorptive) dye may be selected in the group comprising, but not limited to: Lugol's solution, methylene blue, toluidine blue, crystal violet and the like. According to the invention herein disclosed, said non-vital (or contrast) dye may be selected in the group comprising, but not limited to: indigo carmine and the like. According to the invention herein disclosed, said reactive dye may be selected in the group comprising, but not limited to: Congo red, phenol red and the like. Any mixture of the above dyes can be used to form the appropriate pharmaceutical composition. According to a preferred embodiment, said at least one dye is methylene blue. According to another preferred embodiment, said at least one dye is indigo carmine.

According to the invention herein disclosed, said at least one dye is contained in an amount which ranges from about 0.0001% to about 0.2% by weight with respect to the weight of the pharmaceutical composition, preferably from about 0.0002% to about 0.05% by weight with respect to the weight of the pharmaceutical composition, more preferably from about 0.0005% to about 0.01% by weight with respect to the weight of the pharmaceutical composition. Much more preferably, said at least one dye is contained in the composition of the invention in an amount of about 0.001% by weight or 0.002% by weight, with respect to the weight of the composition.

The pharmaceutical composition of the invention herein disclosed may comprise at least one agent characterized by having a trophic activity on the epithelial cells of the gastrointestinal mucosa. Trophic agents are substances capable of promoting cellular growth, differentiation, and survival. In gastrointestinal endoscopy, resectioning procedures such as polypectomy, EMR and ESD are generally not followed by suturing. In other words, once the lesion has been removed by means of one of said procedures, the mucosa is not sutured and the wound is left opened; thus the healing of the wound must occur naturally. In this sense, the incorporation into the pharmaceutical compositions according to the invention of at least one agent proved to possess a trophic activity on the epithelial cells of the gastrointestinal mucosa could be advantageous, since said pharmaceutical compositions could exert a positive, beneficial effect on wound healing, promoting cellular growth and differentiation for faster closure and healing of the surgical wound.

In the preparation of pharmaceutical compositions in form of emulsions or microemulsions according to the invention herein disclosed, said at least one agent characterized by having a trophic activity on the epithelial cells of the gastrointestinal mucosa can be selected in the groups comprising, but not limited to: aminoacids and salts thereof, such as arginine, glutamine, glutamic acid, citrulline, proline, cysteine and the like; short-chain fatty acids (SCFA) and salts thereof, such as acetic acid and salts thereof, propanoic acid and salts thereof, butyric acid and salts thereof, and the like; carbohydrates, such as glucose, fructose, galactose, sucrose, maltose, lactose and the like; polyamines and salts thereof, such as putresceine, spermidine, spermine and the like; fatty acids and salts thereof, such as oleic acid and salts thereof, linoleic acid and salts thereof, mirystic acid and salts thereof, stearic acid and salts thereof and the like; vitamins, such as vitamin A, vitamin $B_2$, vitamin C, vitamin D, and the like. Any mixture of the above agents characterized by having a trophic activity on the epithelial cells of the gastrointestinal mucosa can be used to form the appropriate pharmaceutical composition. In one embodiment, said at least one agent characterized by having a trophic activity on the epithelial cells of the gastrointestinal mucosa is sodium butyrate. In another embodiment, said at least one agent characterized by having a trophic activity on the epithelial cells of the gastrointestinal mucosa is sodium vitamin $B_2$. In a preferred embodiment, said at least one agent characterized by having a trophic activity on the epithelial cells of the gastrointestinal mucosa is glutamic acid.

According to the invention herein disclosed, said at least one agent characterized by having trophic activity on the epithelial cells of the gastrointestinal mucosa is contained in an amount which ranges from about 0.01% to about 5% by weight with respect to the weight of the pharmaceutical composition, preferably from about 0.05% to about 3% by weight with respect to the weight of the pharmaceutical composition, more preferably from about 0.1% to about 2% by weight with respect to the weight of the pharmaceutical composition.

The pharmaceutical composition of the invention herein disclosed may comprise at least one therapeutic agent. In the preparation of pharmaceutical compositions in form of emulsions or microemulsions according to the invention herein disclosed, said at least one therapeutic agent can be selected in the groups comprising, but not limited to: antibiotics, such as penicillins, cephalosporins, aminoglycosides, macrolides, rifamycins, metronidazole and the like; non-steroidal anti-inflammatory drugs, such as ketorolac and salts thereof, indometacin, piroxicam, ketoprofen and salts thereof, and metamizol and salts thereof, and the like; steroidal anti-inflammatory drugs, such as cortisol, prednisolone and esters thereof, methyprednisolone and esters thereof, triamcinolone acetonide, betamethasone and esters thereof, and the like; local anesthetics, such as lidocaine and salts thereof, mepivacaine and salts thereof, bupuvacaine and salts thereof, and the like; vasoconstrictor drugs, such as epinephrine and salts thereof, norepinephrine and salts thereof, and the like. Any mixture of the above therapeutic agents can be used to form the appropriate pharmaceutical composition and to achieve specific therapeutic effects. In an embodiment, said at least one therapeutic agents is a local anesthetic, such as lidocaine hydrochloride. In another embodiment, said at least one therapeutic agent is a vasoconstrictor drug, such as epinephrine hydrochloride. Further in another embodiment, the pharmaceutical composition according to the invention herein disclosed comprise at least one local anesthetic and at least one vasoconstrictor drug, such as lidocaine hydrochloride and epinephrine hydrochloride.

Additionally, at least one physiologically acceptable excipient may be added to the pharmaceutical composition according to the invention herein disclosed to obtain final composition for use in endoscopic procedures provided with suitable characteristics and stability. By way of example, said at least one physiologically acceptable excipient may be selected among antioxidants, chelating agents, preservatives, antimicrobial agents, polymers provided with bioadhesive properties and the like.

The pharmaceutical composition in form of emulsion or microemulsion of the invention herein disclosed may be packaged in primary packaging configurations well known in the art. Suitable primary packaging types can be selected in the groups comprising, but not limited to: ampoules, vials, bottles, pre-filled syringes and the like. In an embodiment, the pharmaceutical composition in form of emulsion or microemulsion of the invention herein disclosed is packaged in 5 mL or 10 mL pre-filled syringes. In a preferred embodiment, the pharmaceutical composition in form of emulsion or microemulsion of the invention herein disclosed is packaged in 10 mL, 20 mL or 50 mL vials. In another preferred embodiment, the pharmaceutical composition in form of emulsion or microemulsion of the invention herein disclosed is packaged in 10 mL, 20 mL or 50 mL ampoules The pharmaceutical composition in form of emulsion or microemulsion of the invention herein disclosed are administered by means of endoscopic injection needles suitable to be inserted in the working channel of an endoscope or gastroscope. In an embodiment, the solution is administered at a temperature below the room temperature, such as below 10° C. In a preferred embodiment, the solution is administered at a temperature ranging from 2° C. to 8° C.

Another aspect of the invention herein disclosed provides a kit for use in an endoscopic procedure, said kit comprising:
a) pharmaceutical composition in form of emulsion or microemulsion according to the invention herein disclosed;
b) an endoscopic injection needle;
c) instruction for use.

In the preparation of said kit, said pharmaceutical composition in form of emulsion or microemulsion according to the invention herein disclosed may be packaged in primary packaging configurations well known in the art. Suitable primary packaging types can be selected in the groups comprising, but not limited to: ampoules, vials, bottles, pre-filled syringes and the like. In an embodiment, in the preparation of said kit, the pharmaceutical composition in form of emulsion or microemulsion of the invention herein disclosed is packaged in 5 mL or 10 mL pre-filled syringes. In a preferred embodiment, in the preparation of said kit, the pharmaceutical composition in form of emulsion or microemulsion of the invention herein disclosed is packaged in 10 mL, 20 mL or 50 mL vials. In another preferred embodiment, in the preparation of said kit, the pharmaceutical composition in form of emulsion or microemulsion of the invention herein disclosed is packaged in 10 mL, 20 mL or 50 mL ampoules. In the preparation of said kit according to the invention herein disclosed, suitable endoscopic injection needles may have a diameter of the needle ranging from 12 gauge to 35 gauge, preferably from 15 gauge to 30 gauge, more preferably from 17 gauge to 28 gauge. In the preparation of said kit according to the invention herein disclosed, suitable endoscopic injection needles may have a length ranging from 100 cm to 300 cm, preferably from 120 cm to 260 cm, more preferably from 140 cm to 250 cm. In the preparation of said kit according to the invention herein disclosed, suitable endoscopic injection needles may have an outer diameter ranging from 1.0 mm to 4.0 mm, preferably from 1.5 mm to 3.0 mm, more preferably from 1.8 mm to 2.5 mm. In the preparation of said kit according to the invention herein disclosed, suitable endoscopic injection needles may be composed of materials selected in the groups comprising, but not limited to: polymers or copolymers, such as polyethylene (PE), polypropylene (PP), polyvinylchloride (PVC), polycarbonate (PC), polytetrafluoroethylene (PTFE), polyethylene terephthalate (PET), polystyrene (PS), polyamide (PA), epoxy resins, polyurethane, polyester, polymethyl methacrylate and the like; rubbers, such as silicone rubber, natural rubber and the like; metals and metal alloys such as aluminum, titanium, iron, chromium, nickel, molybdenum, stainless steel, and the like. Any combination of the above materials may be used to form the appropriate endoscopic injection needle. Endoscopic injection needles suitable for the preparation of the kit according to the invention herein disclosed can be found easily on the market; by way of example, a suitable injection needle can be selected from the marketed injection needles comprising, in a non-limiting way Cook® AcuJect® Variable Injection Needles, Cook® Injectaflow® Variable Injection Needles, Boston Scientific® Interject® Injection Therapy Needles Catheters, G-Flex® Injection Needles, Endo-Flex® Sclerotherapy Needles, ConMed™ Click-Tip™ Injection Needles, Medi-Globe® Injectra® Injection Needle, Olympus® InjectorForce Max™, US Endoscopy™ Articulator™ injection needle, US Endoscopy™ Vari-Safe™ injection needle, Kimberly-Clarck™ injection needle catheters, and the like.

In a preferred application of the invention, the pharmaceutical composition in form of emulsion or microemulsion according to the invention herein disclosed is used in an endoscopic resection procedure by:
a) sucking a volume of emulsion from its primary container by means of a syringe,
b) injecting a suitable volume of said emulsion by means of an endoscopic injection needle inserted in the working channel of the endoscope immediately under the superficial mucosal layer,
c) deposing a liquid volume of some ml, that become a gel cushion having a thickness of few to some millimeters when in place, into the submucosal layer.

The elevation of the mucosal surface operated by the injected composition allow the endoscopist to perform an easy resection of a mucosal lesion found during the execution of the endoscopic procedure even if the lesion is flat and not protruding into the intestinal, esophageal or gastric lumen. The presence of the dye into the gel cushion helps the endoscopist to visualize the structures beneath the mucosa (e.g. the submucosal layer and the muscolaris mucosa), thereby lowering the risk that the endoscopist, performing the resection procedure, may cause damages to said structures: as a matter of facts, the dye make him able to distinguish between the cushion cavity and the mucosal basement. The removal of the lesion from the mucosal surface generates a hole into the basement that has to be healed and the presence, into the pharmaceutical compositions according to the invention herein disclosed, of an agent characterized by trophic activity on the epithelial cells of the gastrointestinal mucosa has the aim of accelerating the healing of the mucosal wound. The persistency of the cushion generated by the injected volume of the pharmaceutical composition in form of emulsion or microemulsion according to the invention herein disclosed is lasting enough to allow the endoscopic resection procedure to be performed without the need to re-inject said composition every couple of minutes, as it generally happens when normal saline solution is used.

Definitions

References in the specification to "one embodiment", "an embodiment" and similar indicate that the described embodiment may include a particular aspect, feature, structure or characteristic. Moreover, such phrases may, but do not necessarily, refer to the same embodiment referred to in other portions of the specification. Further, when a particular aspect, feature, structure or characteristic is described in connection with an embodiment, it is within knowledge of a person skilled in the art to affect or connect said aspect, feature, structure or characteristic with other embodiments, whether or not explicitly described.

The singular forms "a", "an" and "the" include plural references unless the context clearly dictates otherwise.

Thus, for example, a reference to "a compound" includes a plurality of such compounds. It is further noted that the claims may be drafted to exclude any optional element. As such, this statement is intended to serve as antecedent basis for the use of exclusive terminology, such as "soley", "only", and the like, in connection with the recitation of claims elements or use of a "negative" limitation.

The term "and/or" means anyone of the items, any combination of the items, or all the items with which this term is associated.

The terms "comprising", "having", "including" and "containing" are to be construed as open-ended terms (i.e. meaning "including, but not limited to") and are to be considered as providing support also for terms as "consist essentially of", "consisting essentially of", "consist of" or "consisting of".

The terms "consist essentially of", "consisting essentially of" are to be construed as a semi-closed terms, meaning that no other ingredients which materially affects the basic and novel characteristics (and optionally physiologically acceptable excipients and/or adjuvants) of the invention are included.

The terms "consists of", "consisting of" are to be construed as a closed term.

PEG: Polyethylene glycol.

Unless indicated otherwise herein, the term "about" is intended to include values, e.g. weight percentages, proximate to the recited range that are equivalent in terms of the functionality of the individual ingredient, the composition, or the embodiment.

A person skilled in the art will recognize that, for any and all purposes, particularly in terms of providing a written description, all ranges recited herein also encompass any and all possible sub-ranges and combinations of sub-ranges thereof, as well as the individual values making up the range, particularly integer values. A recited range includes each specific value, integer, decimal, or identity within the range.

A person skilled in the art will recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of anyone or more of members of a recited group. Accordingly, provisos may apply to any of the disclosed categories or embodiments whereby anyone or more of the recited elements, species, or embodiments, may be excluded from such categories or embodiments, for example, as used in an explicit negative limitation.

The term "Emulsion" refers to a heterogeneous preparation composed of two immiscible liquids (by convention described as oil and water), one of which is dispersed as fine droplets uniformly throughout the other. The phase present as small droplets is called the disperse, dispersed, or internal phase and the supporting liquid is known as the continuous or external phase. Emulsions are conveniently classified as oil-in-water (o/w) or water-in-oil (w/o), depending on whether the continuous phase is aqueous or oily. Multiple emulsions, which are prepared from oil and water by the reemulsification of an existing emulsion so as to provide two dispersed phases, are also of pharmaceutical interest. Multiple emulsions of the oil-in-water-in-oil (o/w/o) type are w/o emulsions in which the water globules themselves contain dispersed oil globules; conversely, water-in-oil-in-water (w/o/w) emulsions are those where the internal and external aqueous phases are separated by the oil. "Microemulsions" are thermodynamically stable, transparent (or translucent) dispersions of oil and water that are stabilized by an interfacial film of surfactant molecules. The surfactant may be pure, a mixture, or combined with a cosurfactant such as a medium-chain alcohol. Microemulsions are readily distinguished from normal emulsions by their transparency, their low viscosity, and more fundamentally their thermodynamic stability and ability to form spontaneously. The dividing line, however, between the size of a swollen micelle (~10-140 nm) and a fine emulsion droplet (~100-600 nm) is not well defined, although microemulsions are very labile systems and a microemulsion droplet may disappear within a fraction of a second whilst another droplet forms spontaneously elsewhere in the system. The above definitions of "emulsion" and "microemulsion" were taken from "Encyclopedia of Pharmaceutical Technology", $3^{rd}$ edition, Informa Healtcare.

The term "endoscopic mucosal resection" (EMR) refers to an endoscopic technique developed for removal of sessile or flat neoplasms confined to the superficial layers (mucosa and submucosa) of the GI tract. The term "endoscopic mucosal dissection" (ESD) refers to an endoscopic technique developed specifically for removing larger lesions.

"Endoscopic injection needles", known also under the names "injection needles" or "injection needle catheters" or "endoscopic injection needle catheters", are devices which can be long up to about 230 cm and which include a relatively long catheter within which an inner injection tube having a distal injection needle is slideably disposed. Generally, a proximal actuating handle is coupled to the catheter and the injection tube for moving one relative to the other when necessary. The needle is generally retractable. Fluid access to the injection tube is typically provided via a luer connector on the handle. Endoscopic injection needle devices are typically delivered to the injection site through the working channel of the endoscope. In order to protect the lumen of the endoscope working channel from damage, the handle of the infusion needle device manipulated to withdraw the distal injection needle into the lumen of the catheter before inserting the device into the endoscope. This is important to prevent exposure of the sharp point of the injection needle as the device is moved through the lumen of the endoscope. When the distal end of the endoscopic injection needle device is located at the injection site, its handle is again manipulated to move the injection needle distally out of the lumen of the catheter. When advanced to the most distal position, the exposed portion of the injection needle is approximately 4-6 mm in length.

The "viscosity" defines the resistance of a liquid or semisolid against flow. The flow of liquids or semisolids is described by viscosity, or, more precisely, by shear viscosity η. The shear viscosity of a fluid expresses its resistance to shearing flows, where adjacent layers move parallel to each other with different speeds. Common units of measurement of viscosity are the pascal-second (Pa·s), the poise (P) and cP (centipoises).

"Body temperature" refers to the level of heat produced and sustained by the body processes. Heat is generated within the body through metabolism of nutrients and lost from the body surface through radiation, convection, and evaporation of perspiration. Heat production and loss are regulated and controlled in the hypothalamus and brainstem. Normal adult body temperature, as measured orally, is 37° C., even though little variations are normally recorded throughout the day.

"Room temperature" (RT) is generally defined as the ambient air temperature in whatever environment being used for a given procedure. More specifically, it is defined as 20-25° C., as some ambient temperatures, by nature, do not fall within this range. Generally, protocols calling for steps to be performed at RT require that temperatures do not fall below 18° C., and do not exceed 27° C.

"In (or under) laboratory test conditions" or "in laboratory conditions" or "in laboratory tests", as used herein, refer to in-vitro conditions, such as methods, equipment and instruments commonly used in laboratory tests to perform a physical-chemical characterisation of a composition. The term refers to methods, equipment and instruments used and performed in laboratory.

"Critical Gelation Concentration" (CGC), for a solution of inverse thermosensitive polymer, is the concentration of said polymer above which said solution is able to transition from a liquid phase to a gel phase in response to the raise in temperature.

"Critical Gelation Temperature" (CGT) represents the temperature above which a solution containing an inverse thermosensitive polymer at a concentration equal to or above the critical gelation concentration transitions from a liquid phase to a gel phase.

"Lugol's solution": is a solution of elemental iodine and potassium iodide in water.

"cP": centipoises, unit for measuring viscosity.

The following examples are included for purpose of illustration of certain aspects and embodiments of the invention, and are not intended to limit the invention.

Experimental Part

The pharmaceutical compositions of the examples 1 and 2 were fully studied and characterized in laboratory as regards:
flowability;
viscosity.

For both the tests, a 15% solution of poloxamer 407 in normal saline, having the composition detailed here below was used as reference:

| Component | g/100 g |
|---|---|
| Sodium chloride | 0.9000 |
| Poloxamer 407 | 15.0000 |
| Water for injection | q.s. 100.0 g |

Flowability Measurement

The measurements of the flowability of the compositions of Examples 1 and 2 and of the reference were performed using a Melab® Computer Aided Penetration Load Measuring Station Deka 8 composed of: a testing unit (s/n: DKA 0304-1), a transferring unit with controlled DC-drive and linear guiding linear scale, a high precision load cell 0-200 N (s/n: K 2633563), a syringe support and a plunger pusher support and measuring electronics. The measurement were performed using 10 mL syringes with a male Luer-Lok fitting connected to Olympus® Injector Force Max® endoscopic injection needles (part number: NM-400U-0523, length: 230 cm, needle diameter: 23 gauge, needle length: 5 mm). Before the measurement, the tested compositions and the reference were kept at 5° C.±3° C.; the measurements of flowability were made using the cold compositions. For each composition, three measurements were recorded. The following tables reports the maximum load of each tested composition as well as of the reference, expressed in Newton (mean of three measurements).

| Composition | Maximum load (mean of 3 measurements) (N) |
|---|---|
| Reference (Poloxamer 407 15% in normal saline) | 90 |
| Composition of Example 1 | 76 |
| Composition of Example 2 | 65 |

The compositions of Example 1 and of Example 2 in form of emulsion have a lower resistance to injection and thus a better flowability through the endoscopic injection needle than the reference, as their maximum load, expressed in Newton (N), is lower than the reference. The effect is accentuated if the content of oily phase of the emulsion is increased, since the composition of Example 2 has a lower resistance to injection and thus a better flowability than the composition of Example 1. The results are shown in FIG. 1.

Viscosity Measurement

The viscosities of the pharmaceutical compositions according to Examples 1 and 2 were measured in laboratory conditions at three different temperatures: T=25° C., T=30° C. and T=37° C. The measurements were performed using a Brookfield LVDV-III Ultra Programmable Rheometer™ equipped with a Brookfield Small Sample Adapter™ device. The Brookfield Small Sample Adapter™ comprised a sample chamber which fitted into a water jacket so that precise temperature control was achieved by means of a circulating thermostating water bath. For the measurements, two different spindles were used, depending upon the viscosity value: for low viscosity values (registered at T=25° C. and T=30° C.), Brookfield™ spindle N. 31 was used; for high viscosity values (registered at T=37° C.), Brookfield™ spindle N. 25 was used.

The viscosities of the solutions are reported in the table below:

| | Viscosity (cP) | | |
|---|---|---|---|
| Composition | Viscosity at 25° C. | Viscosity at 30° C. | Viscosity at 37° C. |
| Reference (Poloxamer 407 15% in normal saline) | 27.2 | 31.3 | 1220.3 |
| Composition of Example 1 | 27.1 | 31.6 | 1236.7 |
| Composition of Example 2 | 27.3 | 31.5 | 1243.7 |

The reference solution and the compositions of Example 1 and of Example 2 showed a gel-forming ability upon heating at body temperature (i.e. 37° C.) in laboratory conditions, passing from the liquid state, having a viscosity of about 27 cP, to the gel state, having a viscosity over 1000 cP. The presence of the oily phase in the compositions of Example 1 and of Example 2 does not alter the characteristic reversible gelling property of the inverse thermosensitive polymer solutions.

EXAMPLES

Example 1

| Component | g/100 g |
|---|---|
| Methylene blue | 0.0010 |
| Sodium chloride | 0.9000 |
| Poloxamer 407 | 15.0000 |
| Soybean oil | 0.0800 |
| Glycerol | 0.0025 |
| Egg lecithin | 0.0120 |
| Sodium oleate | 0.0003 |
| Water for injection | q.s. 100.0 g |

The manufacture of the composition is described hereinafter (for 10.00 Kg of final composition):

a. In a suitable vessel provided with a stirrer, about 8000 mL of water for injection are loaded; then, 90.00 g of sodium chloride are added. The mixture is kept under stirring until a complete dissolution is achieved. The obtained solution is cooled at a temperature ranging between 5° C. and 10° C.; then, 1500.00 g of poloxamer 407 are added under stirring. The mixture is kept under stirring until a complete dissolution is achieved.

b. In a suitable vessel provided with a stirrer, about 181 mL of water for injection are loaded; the temperature is raised at 80° C. 1.20 g of egg lecithin, 0.25 g of glycerol, 0.03 g of sodium oleate are added under stirring. The stirrer is operated until a complete homogenization; then, 8.00 g of soybean oil are added. The mixture is kept at T=80° C. under stirring until an homogeneous emulsion is obtained. The emulsion is then cooled at a temperature below 30° C.

c. The emulsion obtained in step b) is added to the mixture obtained in step a) under stirring. Then, 0.10 g of methylene blue are added under stirring. The mixture is kept under stirring until homogeneity.

d. The pH of the mixture of step c) is measured and it is brought, if necessary, within the range 5.0-7.0.

e. The mixture is brought to a final weight of 10.00 Kg by adding water for injection.

f. The final composition is filtered through a 0.45 μm filter and is packed in 20 mL vials capped with rubber caps and aluminum rings. The vials are sterilized at 121° C. for 20 minutes.

Example 2

| Component | g/100 g |
|---|---|
| Methylene blue | 0.0010 |
| Sodium chloride | 0.9000 |
| Poloxamer 407 | 15.0000 |
| Soybean oil | 0.1600 |
| Glycerol | 0.0050 |
| Egg lecithin | 0.0240 |
| Sodium oleate | 0.0006 |
| Water for injection | q.s. 100.0 g |

The composition was obtained by a process similar to that described in Example 1.

Example 3

| Component | g/100 g |
|---|---|
| Methylene blue | 0.0010 g |
| Sodium chloride | 0.9000 g |
| L-Glutamic acid | 1.0000 g |
| Poloxamer 188 | 18.000 g |
| Soybean oil | 0.1600 g |
| Glycerol | 0.0050 g |
| Egg lecithin | 0.0240 g |
| Sodium oleate | 0.0006 g |
| Sodium hydroxide | q.s. to bring the pH within 5.0 and 7.0 |
| Water for injection | q.s. to 100.0 g |

The manufacture of the composition is described thereinafter (for 10.00 Kg of final composition):

a) In a suitable vessel provided with a stirrer, about 6000 mL of water for injection are loaded; then, 90.00 g of sodium chloride are added. The mixture is kept under stirring until a complete dissolution is achieved. The obtained solution is cooled at a temperature ranging between 5° C. and 10° C.; then, 1800.00 g of poloxamer 188 are added under stirring. The mixture is kept under stirring until a complete dissolution is achieved.

b) In a suitable vessel provided with a stirrer, about 181 mL of water for injection are loaded; the temperature is raised at 80° C. 2.40 g of egg lecithin, 0.50 g of glycerol, 0.06 g of sodium oleate are added under stirring. The stirrer is operated until a complete homogenization; then, 16.00 g of soybean oil are added. The mixture is kept at T=80° C. under stirring until an homogeneous emulsion is obtained. The emulsion is then cooled at a temperature below 30° C.

c) The emulsion obtained in step b) is added to the mixture obtained in step a) under stirring. Then, 0.10 g of methylene blue and 100.00 g of L-glutamic acid are added under stirring. The mixture is kept under stirring until homogeneity.

d) The pH of the mixture of step c) is measured and it is brought within the range 5.0-7.0 by adding 10% NaOH in water for injection.

e) The mixture is brought to a final weight of 10.00 Kg by adding water for injection.

f) The final composition is filtered through a 0.45 μm filter and is packed in 20 mL vials capped with rubber caps and aluminum rings. The vials are sterilized at 121° C. for 20 minutes.

Example 4

| Component | g/100 g |
|---|---|
| Methylene blue | 0.0010 |
| Sodium chloride | 0.9000 |
| Poloxamer 188 | 10.0000 |
| Soybean oil | 0.1600 |
| Glycerol | 0.0050 |
| Egg lecithin | 0.0240 |
| Sodium oleate | 0.0006 |
| Water for injection | q.s. 100.0 g |

The composition was obtained by a process similar to that described in Example 3.

The invention claimed is:

1. A method of performing an endoscopic procedure which comprises injecting a pharmaceutical composition in the form of an emulsion or microemulsion through an endoscopic injection needle without the need to use a high pressure generating device to a target tissue of a subject to form a submucosal cushion, the pharmaceutical composition comprises
- (a) an aqueous phase;
- (b) an oily phase;
- (c) at least one surfactant;
- (d) at least one co-surfactant;
- (e) at least one inverse thermosensitive polymer; and
- (f) optionally at least one physiologically acceptable excipient;

wherein said at least one inverse thermosensitive polymer has not been purified to reduce polydispersity of the molecular weight of said at least one inverse thermosensitive polymer, wherein said at least one inverse thermosensitive polymer present in the pharmaceutical composition has a concentration equal to or above a critical gelation concentration, wherein the concentration of said at least one inverse thermosensitive polymer in the pharmaceutical composition has a critical gelation temperature of about 37° C., wherein said pharmaceutical composition flows through the endoscopic injection needle at room temperature without the need to use a high pressure generating device, wherein said pharmaceutical composition flows more freely through an endoscopic injection needle compared to a similar aqueous pharmaceutical composition as measured by a lower maximum load expressed in Newtons correlating to lower resistance to injection and better flowability, and wherein said pharmaceutical composition gels and forms a cushion when injected into the target tissue at about 37° C.

2. The method of claim 1, wherein said at least one inverse thermosensitive polymer is selected from poloxamer 124, poloxamer 188, poloxamer 237, poloxamer 338, poloxamer 407 and mixtures thereof.

3. The method of claim 1, further comprising at least one dye selected from a vital dye, a non-vital dye, a reactive dye and mixtures thereof.

4. The method of claim 1, wherein said oily phase comprises at least one lipophilic compound.

5. The method of claim 4, wherein said at least one lipophilic compound is selected from natural oils, fatty acid esters, fatty alcohols, fatty acids and mixtures thereof.

6. The method of claim 4, wherein said at least one lipophilic compound is selected from soybean oil and medium-chain triglycerides.

7. The method of claim 1, wherein said at least one surfactant is selected from the group consisting of a non-ionic surfactant, an ionic surfactant and mixtures thereof.

8. The method of claim 7, wherein said non-ionic surfactant is selected from polysorbate 80 and PEG-15 hydroxystearate.

9. The method of claim 7, wherein said ionic surfactant is selected from egg lecithin, hydrogenated phosphatidyl choline from egg lecithin, soybean lecithin and hydrogenated soybean lecithin.

10. The method of claim 1, wherein said co-surfactant is selected from propylene glycol, glycerol and sodium oleate.

11. The method of claim 1, wherein said co-surfactant is a mixture of glycerol and sodium oleate.

12. The method of claim 1, wherein said cushion is subjected to a resection procedure.

13. The method of claim 12, wherein said resection procedure is an endoscopic procedure selected from a polypectomy, an endoscopic mucosal resection (EMR) and/or an endoscopic submucosal dissection (ESD).

14. The method of claim 12, wherein the resection procedure is performed during a gastrointestinal endoscopy.

15. The method of claim 13, wherein the resection procedure is performed during a gastrointestinal endoscopy.

16. The method of claim 1, wherein said endoscopic procedure is performed in the esophagous, stomach, small intestine, cecum, colon, sigmoid colon and/or rectum.

17. The method of claim 1, wherein said at least one inverse thermosensitive polymer is contained in an amount between about 2% and about 30% by weight, with respect to the weight of the composition.

18. The method of claim 1, wherein said at least one inverse thermosensitive polymer is contained in an amount between about 5% and about 25% by weight, with respect to the weight of the composition.

19. The method of claim 1, wherein said at least one inverse thermosensitive polymer is contained in an amount between about 8% and about 20% by weight, with respect to the weight of the composition.

* * * * *